United States Patent
Biscotti et al.

(10) Patent No.: US 11,547,656 B2
(45) Date of Patent: Jan. 10, 2023

(54) CRYOGENIC NATURAL SKIN CARE COMPOSITIONS AND CORRESPONDING METHODS

(71) Applicants: Luz Sarmiento Biscotti, Shelton, CT (US); Suzanne Biscotti, Worcester, MA (US)

(72) Inventors: Luz Sarmiento Biscotti, Shelton, CT (US); Suzanne Biscotti, Worcester, MA (US)

( * ) Notice: Subject to any disclaimer, the term of this patent is extended or adjusted under 35 U.S.C. 154(b) by 71 days.

(21) Appl. No.: 16/888,118

(22) Filed: May 29, 2020

(65) Prior Publication Data
US 2020/0375885 A1 Dec. 3, 2020

Related U.S. Application Data

(60) Provisional application No. 62/855,053, filed on May 31, 2019.

(51) Int. Cl.
| | |
|---|---|
| A61K 8/9789 | (2017.01) |
| A61K 8/9794 | (2017.01) |
| A61K 8/06 | (2006.01) |
| A61K 8/36 | (2006.01) |
| A61K 8/92 | (2006.01) |
| A61Q 19/10 | (2006.01) |
| A61Q 19/00 | (2006.01) |
| A45D 40/00 | (2006.01) |

(52) U.S. Cl.
CPC ........ *A61K 8/9789* (2017.08); *A45D 40/0068* (2013.01); *A61K 8/06* (2013.01); *A61K 8/361* (2013.01); *A61K 8/922* (2013.01); *A61K 8/9794* (2017.08); *A61Q 19/008* (2013.01); *A61Q 19/10* (2013.01); *A45D 2040/0012* (2013.01); *A45D 2200/15* (2013.01)

(58) Field of Classification Search
None
See application file for complete search history.

(56) References Cited

U.S. PATENT DOCUMENTS

| | | | |
|---|---|---|---|
| 6,656,484 B1 * | 12/2003 | Lube | ........................ A61Q 3/02 132/73 |
| 10,111,919 B2 | 10/2018 | Florence | |
| 10,123,988 B2 | 11/2018 | Donello et al. | |
| 10,130,673 B2 | 11/2018 | Gan et al. | |
| 2004/0022818 A1 * | 2/2004 | Cho | ...................... A61K 8/9794 424/769 |
| 2013/0164265 A1 * | 6/2013 | Flavin | .................. A61K 9/0014 424/773 |
| 2015/0320031 A1 * | 11/2015 | Andreasen | ........... A01N 1/0221 435/1.3 |
| 2017/0020949 A1 * | 1/2017 | Gan | ...................... A61K 36/185 |

FOREIGN PATENT DOCUMENTS

WO    WO 2019/113097 A2 *  6/2019

OTHER PUBLICATIONS

Kate Somerville, webpage, skin health experts https://www.katesomerville.com/anti-aging-products-tightn-cryogenic-skin-tightening-gel?utm_source=google&utm_medium=cpc&utm_campaign=shopping&https://ad.atdmt.com/s/go;adv=11292207974468;ec=11292208132163;c.a=71700000043664670;s.a=GOOGLE;p.a=71700000043664670;as.a=58700004580538082; 4 pages Jan. 11, 2017.
E3Live, fresh frozen superfoods https://www.e3live.com/c-2-fresh-frozen-superfoods.aspx, 1 page Oct. 9, 2014.
Sunfood, super foods https://www.sunfood.com/personal-care-supplements/skin-care.html 1 page, Jan. 1, 2015.
Insider Reviews, superfood skincare line https://www.businessinsider.com/youth-to-the-people-review-vegan-clean-skin-care-2018-8 7 pages, Aug. 20, 2020.
The beauty industry generates a lot of plastic waste. Can it change? https://www.nationalgeographic.com/environment/2019/04/beauty-personal-care-industry-plastic/#close 5 pages, Apr. 18, 2019.
Aloe—Mayo clinic https://www.mayoclinic.org/drugs-supplements-aloe/art-20362267, 3 pages Jul. 27, 2017.
Skin Icing: How This Chilly Facial Beautifies Skin https://www.byrdie.com/skin-icing-how-this-chilly-facial-beautifies-skin-2442895 18 pages, Jun. 3, 2019.

* cited by examiner

*Primary Examiner* — David J Blanchard
*Assistant Examiner* — Sarah J Chickos
(74) *Attorney, Agent, or Firm* — UConn IP Law Clinic; Thomas J. Kennedy, III; Keren Blaunstein (57) ABSTRACT

A skin treatment composition is described comprising a cryopreserved blend of natural materials including at least two components selected from the group consisting of wheat grass juice, wheat grass pulp, shea butter, cocoa powder, rice flour, coffee, jojoba oil, hemp oil, castor oil, and sugarcane juice. The skincare treatment composition is applied with a specialty applicator that is frozen into the compound during processing. Methods of making, packaging and using the compositions also are disclosed.

20 Claims, 5 Drawing Sheets

CRYOGENIC NATURAL SKIN CARE COMPOSITIONS AND CORRESPONDING METHODS

CROSS-REFERENCE TO RELATED APPLICATIONS

This application claims the benefit of, and priority to, US Provisional Patent Application No. 62/855,053 filed May 31, 2019, the contents of which are incorporated by reference herein in their entirety.

BACKGROUND

The panoply of skin creams, cosmetic, and dermal treatments available today to the consumer run the range of regenerative therapeutics to moisturizing creams to natural emollients.

Many of these materials contain ingredients that have a shelf life and are susceptible to degradation/oxidation with time. This is especially true with natural ingredients that are incorporated in to these skin treatments.

Many times, preservatives, such as antioxidants, are utilized to preserve the integrity of the degradation susceptible components of the treatments or cosmetics. The use of artificial preservatives, however, detracts from both the efficacy and desirability of these formulations.

The retarding and/or preservation of these natural ingredients without the use of preservatives is therefore a desirable goal.

It is also a desirable goal to have a specialty applicator that may be associated with the container and used by the end-user of the skincare compound for effective application of the skincare compound to the end user's skin.

The human skin is the largest sensory organ, it absorbs 70% of what it's put on it through the pores creating biochemical reactions in the body. Skin absorption relates to the degree of exposure to and possible effect of a substance which may enter the body through the skin. The skin undergoes constant renewal, every 28 days all cells are turned over as the most superficial cells are replaced by new ones. The bio-chemical composition of the human skin are proteins, vitamins, minerals and fats found in plants. The regenerative properties of plants have grabbed the interest of dermatology researchers and the cosmetics industry.

Plant-based cosmetics have their own disadvantages, such as difficulties in cell culture. Although research on plant stem cells used in skin care reveals their potential as skin protectives, antiaging and antiwrinkle products, the actual stem cells in conventional cosmetic formulations are already dead. Claimed benefits of smooth and firm skin are due to antioxidants and active extracts from stem cells.

SUMMARY

The present disclosure relates, in various embodiments, to the use of natural ingredients that are incorporated into skin creams, skin lotions, cosmetics, and dermal treatments, collectively known as skin treatments, where the natural ingredients are preserved through the use of cryogenic or flash freezing techniques.

The natural ingredients consist of long chain fatty acids, both saturated and unsaturated, vitamins, antioxidants, natural materials, "superfood" compounds and various mineral complexes. These may or may not be compounded into more complex carbohydrates, starches and fats such as sugarcane juice, rice flour, cocoa powder, castor oil, hemp oil, and other naturally derived materials.

Live cells are likely to be more advantageous, which raises a need for research in delivery methods. There are catalyst plants that increase the rate of bio-chemical reactions on the skin and inside the body.

The utilization of specific mixtures of materials are necessary to assure that cryogenically or flash frozen preserved skin treatment natural ingredients maintain their integrity in the frozen formulations. Some of these cryopreservatives may include glycerol, and simple and complex sugars.

One embodiment disclosed herein is a skin treatment composition comprising: a blend of base materials, natural ingredients, including at least one of wheat grass juice, wheat grass pulp, shea butter, cocoa powder, rice flour, coffee grains, jojoba oil, hemp oil, castor oil, and sugarcane juice, and a cryopreservative such that the natural ingredient's integrity is not diminished when the skin treatment is frozen. In some cases, the cryopreservative is a long chain fatty acid. In embodiments, the composition of composition is an emulsion. In embodiments, the cryopreservative is naturally occurring. In embodiments, the flour is brown rice flour.

Materials such as brown rice provide nutrients, stability and exfoliating action to the composition. Brown rice is a natural wholesome food rich in essential minerals such as manganese, iron, zinc, phosphorous, calcium, selenium, magnesium and potassium. Vitamin B1 (thiamine), vitamin B2 (riboflavin), vitamin B3 (niacin), vitamin B6, folate, vitamin E (alpha-tocopherol) and vitamin K. The rice and yogurt made with rice provides probiotics and improves stability, viscosity and the thickening. The rice flour serves as a soft and gentle rice flour scrub that can treat hyperpigmentation and blemishes on the face, and smooth's fine lines and wrinkles in the skin. The brown rice and its derivatives has firming and lifting properties. It has oil absorbing properties which help to keep skin clear. Rice Flour scrub acts as a good anti-inflammatory and skin whitening agent.

Another embodiment is a skin treatment composition comprising a cryopreserved blend of natural plant-based materials including at least two components selected from the group consisting of wheat grass juice, wheat grass pulp, shea butter, cocoa powder, rice flour, coffee, jojoba oil, hemp oil, castor oil, and sugarcane juice.

Another embodiment is a method of formulating a skin treatment where the ingredients of the composition include natural ingredients that are cryopreserved or flash frozen.

Yet another embodiment is a method of making the composition containing one or more of the natural ingredients described above, wherein the natural ingredients are blended with a cryopreservative.

A further embodiment is a skincare composition comprising a natural exfoliating material such as ground coffee, wherein the natural exfoliating material has a texture that facilitates the removal of surface materials from the skin. In embodiments, the surface materials include at least one of long-chain natural oils, dead skin cells, surface dirt and other easily removed materials. In some cases, the composition is an emulsion. In embodiments, the composition is flash frozen.

Yet another embodiment is an applicator for a skin treatment composition, wherein the applicator comprises a dispensing portion configured to have the skin treatment material attached thereto in frozen form, and a handle portion comprising cork connected to the applicator. In some cases, the handle portion is stored inside a container having a lid. In addition to the ingredients mentioned above, in embodiments, the composition may contain one or more of strawberry, citrus, Spirulina Powder, Rose water, Pumpkin puree, cinnamon, nutmeg, ginger, turmeric, collagen, yogurt, apples, and salt (NaCl).

Another embodiment is an applicator for a skin treatment composition, wherein a description of the composition is affixed to a lid for the container on the opposite side of the lid from the applicator.

A further embodiment includes the use of wheatgrass juice and wheatgrass pulp that is the product of high-energy mixing and sharing of wheatgrass utilizing a high-speed and/or high torque blender.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The use of ingredients such as wheat grass, coffee grains, cocoa powder, shea butter, and rice flour produce specialized compositions for skin treatments that may be cryogenically preserved or flash frozen. The cryopreservation process begins at room temperature. The wheatgrass is juiced in a high speed and/or high shear mill, also known as a juicer. the extract, such as juice, and the pulp are separated and the pulp is cut in very small pieces. In one embodiment, the pulp and extract, such as juice, are blended together with rose and rice water. The rest of the ingredients are blended and the mix is put in the freezer for ½ an hour at 32° F. (0° C.). The mix is taking out of freezer and mixed again to a milkshake consistency or 100 cPs to 30,000 cPs. The mix is put into molds and flash frozen at 14° F. (−10° C.). For transportation, the product is put in a freezer at −109.3 degrees Fahrenheit (−78.5 degrees C.) for 2 to 3 hours. At the time of packaging the product is put in an insulated thermo box and shipped with ½ of the thermo box filled with dry ice. The product is allowed to warm to 32° F. (0° C.) after 24 hours. The user is then directed to put product in their home freezer 3 hours prior to applying. (The same process is applicable for vegetables and fruits as follows)

The other products made with fruits and vegetables are mix and blend. The mix is put in the freezer for ½ an hour at 32° F. (0° C.). The mix is taking out of freezer and mixed again to a milkshake consistency or 100 cPs to 30,000 cPs. The mix is put into the molds and flash frozen at 14° F. (−10° C.). For transportation, the product is put in a freezer at −109.3° F. (−78.5° C.) for 2 to 3 hours prior to shipment. At the time of packaging, the product is put in an insulated box and shipped with ½ volume of dry ice. The product will return to 32° F. (0° C.) after 24 hours. The user is directed to put product in their home freezer 3 hours prior to applying.

In embodiments, the ingredients in the compositions are organic and/or are grown in a sustainable manner.

These materials may be emulsified together so as to provide a consistent mixture of the skincare ingredients. The emulsification may be carried out through high-speed mixing and the addition of hydrophilic and hydrophobic compounds that form an oil in water or water in oil emulsion.

Coffee grains work as a scrub and exfoliator, smooth, and soften the skin naturally.

A high-speed blender is utilized to micronize fruit pulp and seeds. This mixture acts as both a skin treatment and an exfoliant. Fruits that may be utilized for this process, particularly as a exfoliant, include watermelon pulp and watermelon seeds, strawberry pulp and strawberries seeds, wheatgrass and wheatgrass pulp and coffee. Other non-limiting examples of suitable exfoliant materials include table salt, flour, and baking soda. In some embodiments, the exfoliator is ground to the be the particle size of table salt or corn meal. In some cases, the exfoliant is micronized.

Cocoa Butter is a particularly favorable component to use with shea butter as additive because of its consistency. Cocoa butter is made from the top layer left floating after making the chocolate drink. It was a magical drink considered divine by some cultures. The "Food of the Gods", as the material is sometimes known, is to be used in only the most important social celebrations by the Mayans and Aztecs in Central America 2000 years ago. The butter was used to protect the skin against the sun. Cocoa butter is used for its natural emollient properties as it provides a layer of protection that helps prevent moisture (water) loss from the skin. The essential nutrients in cocoa butter include a high proportion of saturated fats, derived from stearic and palmitic acids. Cocoa butter, unlike cocoa solids, has no more than trace amounts of caffeine and theobromine. Fatty acids like arachidic acid, linoleic acid, oleic acid, palmitic acid, palmitoleic acid, stearic acid, and other fatty acids are in cocoa butter. Cocoa butter also includes phytochemicals, antioxidant, and other anti-inflammatory compounds. These substances may improve blood flow to the skin and slow skin aging by protecting against damage from the sun's harmful UV rays. One common use of cocoa butter is to smooth scars, wrinkles, and other marks on the skin. Cocoa butter has also been promoted to heal rashes from conditions like eczema and dermatitis.

Shea Butter was used by Cleopatra, the Queen of Sheba, and Nefertiti thousands of years ago because of its great properties and benefits for the skin. Shea butter is a fat that comes from the shea tree. It is an emollient which protects, moisturizes and lubricates the skin. It melts at body temperature, penetrates easily into the skin and boosts collagen production, reducing the appearance of wrinkles, stretch marks, acne scars, poison ivy, insect bites, psoriasis and age spots. In foods, shea butter is used as fat for cooking. It is also, widely used in cosmetic products. Shea butter's content of stearic acid makes it easily absorbed into the skin and thus works to moisturize the skin.

Shea butter is a triglyceride (fat) derived from oleic and stearic acid, it also contains linoleic, palmitic and arachidonic acids, vitamin E, vitamin A, and vitamin C.

Some of the effects on the skin include moisturizing the scalp and hair. It also gives a nice "glow" to the skin. Further, it acts as a conditioner agent, making the skin supple by providing hydration. Shea butter also provides anti-aging properties to the skin. Raw shea butter (unprocessed) helps tissue cell regeneration and softening of the skin, which reduces wrinkles. The American Journal of Life Sciences reported a clinical study involving 30 volunteers in which shea butter diminished various signs of aging. In another clinical study for dry, delicate or aging skin, 49 volunteers applied shea butter twice daily and discovered that it prevented ultra violet ("photo") aging. It is also shown to boost collagen production, which is essential for skin strength. The material also relieves windburn, sunburn, and winter dry skin. Raw shea butter is perfect to help eliminate that itchy winter skin through Its moisturizing qualities that penetrate deep into the skin, offering more moisturizing benefits while preventing windburn. It is perfect for cracked and dry heels, hands, rough elbows and knees. It will also reduce stretch marks, scarring and cellulite.

Castor oil has been used by the original settlers since the 1500s because of its Medicinal properties. It was recounted in the Edgar Cayce Health Care Readings. North Carolina State University studies show castor oil is a detoxifier and a cleanser. It is also beneficial for delicate facial skin and is an effective emollient for dry skin. Castor oil increases lymphatic circulation, reduces Inflammation, disinfects the skin and kills bacteria that disrupts skin healthy conditions. Castor oil is a natural emollient that penetrates the skin and helps stimulate the production of collagen and elastin which can soften and hydrate the skin. Therefore, it is a wonderful natural treatment for wrinkles since it restores and rejuvenates skin's natural youthful appearance by making skin smoother, softer and pliant. Essential ingredients in castor oil include ricinoleic acid, oleic acid, linoleic acid, stearic acid, palmitic acid, dihydroxystearic acid, antioxidants, and other fatty acids. Castor oil is a triglyceride of fatty acids and ricinoleic acid. Ricinoleic is not found in any substance other than castor oil—almost 90 percent of its fatty acid content consists of ricinoleic acid. It is also beneficial for delicate facial skin and is an effective emollient for dry skin. As anti-aging—castor oil is packed with antioxidants which are responsible for sweeping away free radicals that cause damage to the skin. With this abundance of antioxidants, the skin remains young looking and wrinkle free. The effects on the face/skin are various. For example, the antimicrobial and anti-inflammatory properties of castor oil make it useful in reducing acne. Ricinoleic acid can inhibit growth in the bacteria that causes acne. Castor oil is also rich in other fatty acids. These can enhance smoothness and softness when applied to facial skin. The fatty acids in castor oil can also promote the growth of healthy skin and improve the complexion. It is also useful and helpful in restoring uneven skin tones. Castor oil has a low comedogenic score. This means it is unlikely to clog pores in the skin and reduces the risk of developing blackheads, making it appropriate for use on sensitive skin. Castor oil contains triglycerides. These can help maintain moisture in the skin, making it a useful treatment for dry skin. Castor oil may have humectant properties, which means that it can draw moisture from the air into the skin, keeping the skin hydrated.

Hemp seed oil, dubbed "nature's most perfectly balanced oil", comes from the seeds of the hemp plant, and offers many health benefits when used topically. It acts as a cleanser, moisturizer, and powerful antioxidant bringing oxygen to the skin and adding a protective layer that helps prevent rashes and relieves acne, eczema, psoriasis, and dry, itchy skin. Essential nutrients include vitamins A, E, and D, potassium, magnesium, iron, zinc, calcium, phosphorus, omega 3 fatty acids, omega 6 fatty acids, 75-80% polyunsaturated fatty acids (the good fats). In general hemp seed oil contains the perfectly balanced 3:1 ratio of Omega 6 (linoleic/LA) to Omega 3 (alpha-linolenic/LNA) essential fatty acids, determined to be the optimum requirement for long-term healthy human nutrition. In reviewing effects on the skin, Hemp oil acts as a cleanser, moisturizer, and powerful antioxidant that helps bring more oxygen to the skin. Giving a healthy, rich complexion making you look young and glowing. It adds a protective layer and aids to relieve acne without clogging the pores. Also, hemp seed oil helps with the discomfort and treatment of eczema, psoriasis, and dry, itchy skin.

Jojoba oil comes from the seeds of a shrub. It is one of the best natural moisturizing and antioxidants for our skin. Jojoba oil has a chemical structure that's very similar to our skin's natural oils, so it's easily absorbed. Native Africans and Americans have used jojoba oil for centuries to protect the skin against harsh temperatures, reduce pain from skin damage, and accelerate healing of wounds. Jojoba oil contains beneficial ingredients, including vitamins A, E, and B complex, chromium, copper and zinc. It has a very high percentage of iodine which gives jojoba oil its power to heal. It contains three fatty acids: erucic, gadoleic and oleic. It also has palmitic acid, stearic acid, arachidic acid, eicosenoic acid, behenic acid, inoceric acid, and nervonic acid. The effects on the skin include moisturizing the skin and hair. Jojoba oil doesn't evaporate like water based moisturizers can. It also contains promotes natural elastin. It balances oil production in the skin and helps strengthen the skin. It reduces skin inflammation. Jojoba oil is slightly waxy and resembles human sebum. It naturally helps your skin to effectively form a barrier to lock in moisture and deliver nutrients deep into the epidermis.

Aloe Vera or "Lily Of The Desert" gel has long been used for its medicinal properties and health benefits as a wound-healer. The aloe gel's best characteristics are its moisturizing effect on the skin and the fact that it leaves a layer on the skin after drying, protecting the wound. Aloe vera is one of the oldest mentioned plants on record due to its different uses. Cleopatra used aloe in her daily skin treatments. In 1944, the Japanese who were exposed to the "A" bomb applied aloe gel to their wounds and reported faster healing and less scaring. The aloe vera plant is one of the most studied herbs in the natural products category. Aloe vera contains over 200 biologically active, naturally-occurring constituents including polysaccharides, vitamins, enzymes, amino acids, and minerals that promote nutrient absorption, aloe vera includes several necessary vitamins: A, C, E, B1, B2, B3, B6 and B12. It also contains calcium and sodium. It further contains a large number of amino acids, minerals, hormones, and acetylcholine. With anti-inflammatory and cooling properties, aloe vera gel is the perfect remedy for sunburned skin. It provides a protective layer to the skin which helps retain moisture. Aloe vera gel has been used as moisturizer as it is best for oily and acne prone skin. It softens the skin without clogging pores because of its abilities to speed up skin cell reproduction, it also lowers inflammation and reduces redness. Aloe vera is also rich in antioxidants and minerals which can help speed healing.

A non-limiting example of a natural superfood formulation that acts as a moisturizer and emollient formulation, along with the process for making the formulation, is shown in Table 1. The percentages in Tables 1-9 are in volume measurements. These may be converted to weight percentages by multiplying the volume by the specific gravity of the various materials. The formulations set forth in Tables 1-9 are alcohol-free.

in a berry form and varies in size. Coffee is cultivated in Latin America, Africa, and Asia. The bean of the coffee plant produces what's known as "The Magical Fruit", discovered in the 11th Century. It was used to make the "Drink of The Gods", thought to have medicinal and energizing properties exclusive for royalty. The coffee grounds work their magic as you glide the mask on your skin, wiping away dead cells, reducing inflammation and revealing your most natural, healthy complexion. Our organic coffee comes from the warm mountains in the heart of Colombia. Riboflavin, vitamin B2, vitamin B5, manganese, potassium, magnesium and niacin B3 are some of the nutrients in coffee. Coffee grains work as scrub and exfoliator to smooth and soften the skin naturally. It improves the skin appearance. Coffee is an antioxidant that may actually slow down the aging process caused by DNA damage. The caffeine in coffee helps to eliminate unwanted oils, preventing clogged pores and making the skin look flawless.

Cocoa powder comes from the seeds of the cacao plant. The scientific name is *Theobroma cacao*. In ancient times it was used to make chocolate food and drinks. Chocolate, or mole, was consider "Food of the Gods" because of its medicinal and valuable properties. As a "divine" drink it was to be used only in the most important social celebrations by the Mayans and Aztecs in Central America 2000 years ago. Then, and today, pure cacao is a valuable commodity. Cacao has nutritious, medicinal, and aphrodisiac properties. Antioxidants, fat, carbohydrates, protein, polyphenols, flavonoids, calcium, magnesium, sulfur, copper, iron, zinc, potassium, oleic acid, fiber, and vitamins E, B2, B1, B5, B3 and B9. Cocoa is rich in antioxidants, protecting the skin from harmful free radicals, while soothing and smoothing sun damaged skin to prevent dryness and the forming of wrinkles.

Other natural materials that are part of the embodiment include apple, cranberry, pomegranate, potato, watermelon, strawberry, lemon, cucumber, Aloe Vera, avocado, mango, papaya, kiwi, banana, blueberry, blackberry, goji berries, grapes, cacao seeds, coffee seeds, raw turmeric, raw ginger, beets, raspberry, coconut, pineapple, mangosteen, peaches, cherries, orange, apricot, pumpkin, purple sweet potato, sweet potato, nectarine, raspberry, plum, grapefruit, fig, pear, blackcurrant, cantaloupe, carambola (star fruit), date

TABLE 1

| LOVE ME - ID #.-005-1232019-5 | Superfood Mix |
|---|---|
| INGREDIENTS:, cocoa butter, shea butter, castor oil, hemp oil, jojoba Oil and *aloe vera*. | Step 1. Melt Cocoa butter in a double boiler. |
| | Step 2. Add shea butter, mix until completely melted. |
| | Step 3. Add cup jojoba, castor and hemp oils |
| FORMULA | Step 4. Add aloe vera and mix with a hand blender |
| 1.5-2.5 cup Cocoa butter | Step 5. Let it cool dawn to room temperature until begins to harden. |
| 0.5-1.5 cup shea butter | Step 6. Blend all the ingredients to make a thick smoothie. |
| ¼-½ cup Jojoba | Step 7. Put into the frozen molds and flash freeze for 3 hours. |
| ¼-½ cup castor | Step 8. Put in a freezer with dry ice free at −109.3° F (−78.5° C.) for 2 to 3 |
| ¼-½ cup hemp oils | hours. For transportation. |
| 0.5-1.5 cup *Aloe* gel | Step 9. Put final lids for distribution |

An important part of skincare is exfoliation of the skin as well as providing antioxidants for the surface of the skin. A unique combination of natural materials and nutrients will invigorate, stimulate, and help maintain optimum skin health. The materials will also remove damage cell, energize, and soften the complexion and gives a glowing super-moisturized look.

One non-limiting example of a material that will act as an exfoliant is coffee. It comes from the fruit of the coffee plant fruit, elderberries, guava, honeydew melon, jack fruit, plum, kumquat, lychee, mulberries, passion fruit, kale, spinach, celery, carrot, and pitaya (dragon fruit).

Another material that has positive effects on the skin is known as rice yogurt, curd rice, masato, or Tamil Kannada. A dish originating from India and also a traditional fermented drink in Colombia, Masato in English is called probiotic yogurt or simply yogurt rice. Rice is a grain used in almost all cultures. It is a staple food mixed with fruits, herbs or vegetables. If fermented, it becomes a probiotic. Sugar can be added to minimize the acidity. Some of the nutrients in the rice are protein, calcium, vitamin D, saturated fat, cholesterol, sodium, potassium, carbohydrates, and sugars. Full of protein, calcium and vitamin D, curd rice for skin improves the complexion. Its anti-inflammatory properties aids in reducing acne. The antioxidants present in this superfood heals dry skin. Because of the lactic acid present in curd rice, it organically exfoliates and moisturizes your skin at the same time.

Rice flour is also important addition to the skincare compounds. Rice dates as far back as 5000 B.C. in China. The cultivation spread throughout the Asian continent, then Greece and areas of the Mediterranean. Europeans spread it to Africa and the Americas. The domestication of rice is considered one of the most important developments in human history. Rice has become an integral part of human life as food and in religious ceremonies. Rice is a grain that contains a number of vitamins and minerals that are important for human health. Rice is use to make cereals desserts, milk, wine and beauty products. It also is use in construction because its durability and strength. As a cereal grain, it is the most widely consumed staple food for a large part of the world's human population, especially in Asia. Rice can be used as an exfoliant, cleanser, toner, and lightener of hyperpigmentation due to sun and age spots. Rice is also used in makeup products. Rice leaves the skin with smooth texture and a porcelain finish. Rice water illuminates, firms, and tightens skin to appear refreshed and reduces pore size, leaving a powdery, soft feeling. Rice water is also good for acne since it reduces redness and clears blemishes and the starch in the water is said to soothe the inflammation of eczema.

Rice contains natural antioxidants like vitamin C, vitamin-A, phenolic and flavonoid compounds, which may minimize free radical damage from age, sun and environment. White rice is about 90 percent carbohydrate, 8 percent protein and 2 percent fat. White rice is a good source of magnesium, phosphorus, manganese, selenium, iron, folic acid, thiamine, and niacin.

Sugar cane juice is extracted from sugar cane. It is widely used in Mexico, Central and South America as a refreshing energy drink. Due to its nutritional composition, sugarcane juice is considered an alkaline superfood that boosts protein levels and helps maintain skin health. Sugarcane has alpha hydroxy acids (AHAs), such as glycolic acid, which helps increase cell turnover and exfoliate the skin to prevent acne build-up. Some of the nutrients in sugarcane juice are potassium, sodium, sugar, vitamin A, calcium, magnesium, the good kind of carbohydrates, protein, iron, and other essential nutrients that make it the ideal ingredient in energy drinks. It is recommended to apply sugar cane juice on your skin as a facemask as an effective anti-aging skin solution that moisturizes the skin and prevents acne. Such mask will reduce acne if you have an acne prone type of skin. Regular use of sugar cane juice will ensure your skin is radiant and smooth.

A manufacturing process and composition are listed in table 2.

TABLE 2

| | |
|---|---|
| MOCHA BUENA-FORMULA ID #.TRE--002-1232019-2 | Base Blend Formula:<br>¼-¾ rice flour<br>¼-¾ rose water<br>1%-5% frankincense essential oil<br>1%-5% myhre essential oil |
| INGREDIENTS: Coffee, Cocoa Powder, Castor oil, Hemp Oil, Rice Yogurt, (Masato) Rice Flour, and Sugar Cane Juice<br>1-4 cups concentrated coffee<br>1-4 cups cocoa powder<br>0.5-2 cup rice yogurt<br>0.5-2 cup Castor oil<br>⅛-¾ cup Hemp oil<br>0.5-2.0 cup sugar cane juice<br>0.5-2.0 cup rice flour | Mocha Buena Mix<br>Step 1. Base Blend<br>Step 2. Mix dry ingredients, coffee grains, cocoa powder<br>Step 3. Mix Castor oil, rice yogurt, hemp oil and sugar cane juice.<br>Step 4. Mix rice flour and liquid black coffee.<br>Step 5. Blend all the ingredients to make a thick smoothie<br>Step 6. Put into the frozen molds and flash freeze for 3 hours.<br>Step 7. Put in a freezer with dry ice free at −109.3° F (−78.5° C.) for 2 to 3 hours. For transportation.<br>Step 8. Put final lids for distribution |

Another formulation is shown in table 3.

TABLE 3

| WHEATGRASS CLEANSER | |
|---|---|
| 35-45% | Wheatgrass |
| 5-15% | Spirulina Powder |
| 15-25% | Rice |
| 5-15% | Rose Water |
| 5-15% | Hemp oil |
| 0.1-1.0% | Myrrh oil |
| 0.1-1.0% | Frankincense oil |

In table 4 there is a formulation for an exfoliator.

TABLE 4

| MOCHA BUENA EXFOLIATOR | |
|---|---|
| 25-35% | Coffee |
| 25-35% | Cocoa powder |
| 10-20% | Rice |
| 5-15% | Castor oil |
| 0.1-1.0% | Hemp oil |
| 5-15% | Sugar cane juice |

Yet another formulation is shown in table 5 for a moisturizer.

TABLE 5

| LOVE ME BUTTER MOISTURIZER | |
|---|---|
| 25-35% | Cocoa butter |
| 25-35% | Shea butter |
| 5-15% | *Aloe* gel |
| 5-15% | Jojoba oil |

TABLE 5-continued

LOVE ME BUTTER MOISTURIZER

| | |
|---|---|
| 5-15% | Castor oil |
| 5-15% | Hemp oil |

Table 6 is a formulation for Bella Serum.

TABLE 6

4. BELLA SERUM

| | |
|---|---|
| 25-35% | Hemp oil |
| 25-35% | Castor oil |
| 25-35% | Jojoba oil |
| 5-15% | Frankincense oil |

A pumpkin mask is shown in table 7.

TABLE 7

PUMPKIN MAGIC MASK

| | |
|---|---|
| 45-55% | Pumpkin puree |
| 10-20% | Sugar juice |
| 5-15% | *Aloe* Juice |
| 5-15% | Rice flour |
| 5-15% | Hemp oil |
| 0.1-1.0% | Cinnamon, Nutmeg, Ginger |

Table 8 shows a turmeric mask.

TABLE 8

TURMERIC MIDAS TOUCH MASK

| | |
|---|---|
| 35-45% | Yogurt |
| 15-25% | Collagen |
| 5-15% | Rice flour |
| 5-15% | Turmeric |
| 5-15% | Sugar cane juice |
| 5-15% | Jojoba oil |

Table 9 is the formulation for a facial peel.

TABLE 9

APPLE JOHNNY PEEL

| | |
|---|---|
| 55-65% | Apples |
| 15-25% | Rice |
| 0.1-1.0% | Shea Butter |
| 0.1-1.0% | Jojoba oil |
| 0.1-1.0% | Lemon |
| 0.1-1.0% | Pinch of salt (NaCl) |

The materials in Table 9 may be used in conjunction with glycolic acid which is effective in removing the outermost layer of dead cells from the complexion, revealing brighter, fresher skin. The glycolic acid helps with skin discoloration, signs of aging like fine lines and wrinkles. Foods that contain glycolic acid and can be used to remove dead cells from the skin include apple, strawberry and blueberry. In embodiments, these acidic materials are left on the skin for several minutes.

A 100% potato purée may be utilized as a healer skin application as well as the 100% aloe vera formulation.

In one aspect of the embodiment, plant stem cells are preserved by the cryo-preservation process. This allows for live plant stem cells to be applied with the skincare treatments.

Figure 1:
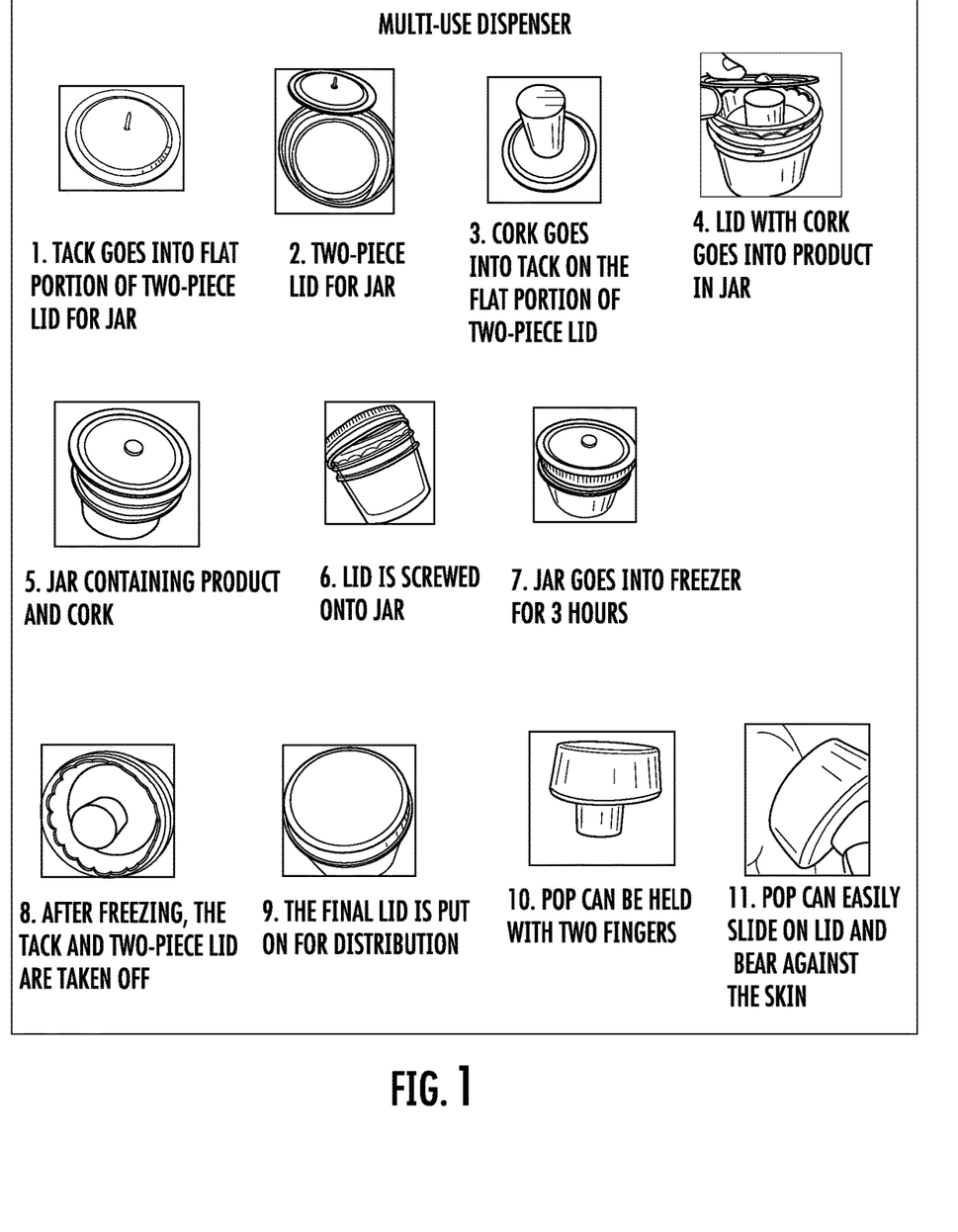
FIG. 1 comprises a set of photographs illustrating a process for adding the natural superfood skincare compounds to a container, along with an applicator that will be frozen into the composition.

FIG. 1 is a depiction of the fill and freezing process, along with a specialty applicator that is frozen into the skincare compounds. Referring to the Figure, in (1), a tack goes into the flat portion of a 2-piece jar lid. In (2) a two-piece jar lid is shown. In (3) a cork goes into the pointed part of the tack on the inside of the lid. In (4) the lid is placed on a jar that contains the skincare composition. The jar with the flat portion of the lid is shown in (5). In (6) the second piece of the two-piece lid is placed on the jar. (7) shows the closed container. The closed container is placed in a freezer. After the skincare composition is frozen, the tack and two-piece lid can be removed as shown in (8). In (9) a final lid is placed on the container for distribution. When a user is ready to use the frozen composition, the applicator with the frozen skincare composition attached thereto is removed from the jar and held by a user, as shown in (10). The "pop," i.e. the applicator with frozen skincare composition attached, can easily slide and bear against skin, as shown in (11). The fill and freezing process includes a cork applicator that is affixed to a lid for the container. In some cases, the cork is mounted to the inner side of the lid, and the outer side of the lid has information describing the skincare compound. Thus, the information is imprinted on the opposite side from the affixed cork applicator. The cork applicator is affixed to the lid of the container prior to being immersed into the skincare compound. The entire container is then frozen. When the skincare compound is to be utilized, the lid is pulled off of the cork applicator which is now frozen into the skincare compound. The cork material acts like a stem that may be grasped to apply the frozen skincare product to the end users skin. The composition is applied to the wearer's skin by moving the outer surface of the frozen composition across the wearer's skin (the outer surface being the surface furthest from the distal end of the handle). The procedure may also be utilized where the original lid or ring is removed and the lid with the contents of the jar attached to the jar and the ring replaced. Also, the applicator does not need to be a cork material. Cork was selected over any other material because of its impermeable, buoyant, elastic properties. Cork is considered sustainable because the cork tree is not cut down to obtain cork; only the bark is stripped to harvest the cork. The tree continues to live and grow for 300 years and, in addition, it is very easy to recycle. It is the most environmentally friendly material and its environmental foot print is very small and clean in computation to wood or any polymer. An alternative to using a pin to hold the cork in the two lid set up would be attaching the cork to the lid using an adhesive or a screw. In this case the lid would became the pop holder/applicator.

Applicator uses: 1. Allows user to hold pop with the fingers. 2. Facilitates application of the product.

Figure 2:
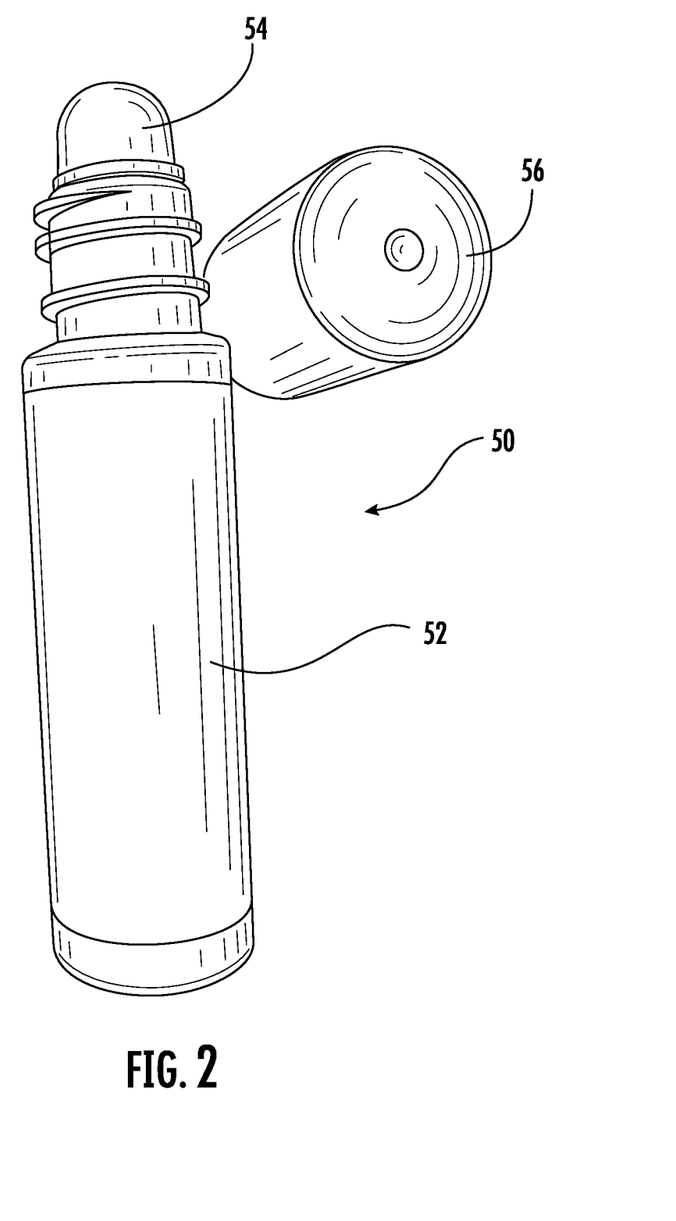
FIG. 2 is a depiction of a roller applicator for applying the skincare materials to the skin.

FIG. 2 shows a roll-on applicator 50 with a container 52, a captured spherical metal roller 54 that may be coated with an applicable formula that is to be applied to the skin, and a lid 56.

Figure 3:
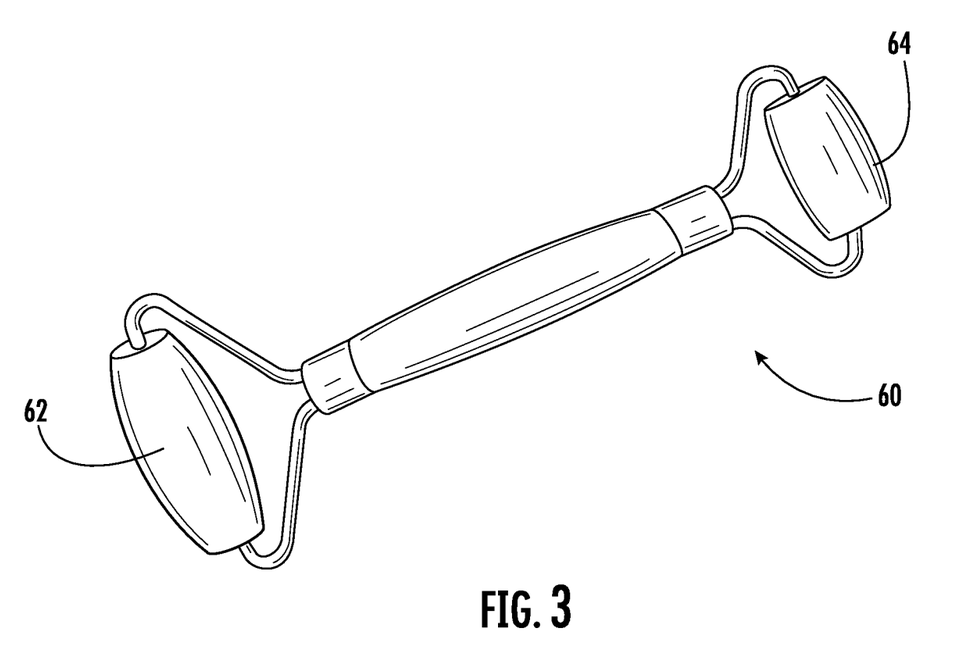
FIG. 3 is a roller applicator with two different types of rollers.

FIG. 3 is a picture of a roll-on applicator 60 comprised of a Jade material with two different sized ends, the bigger end 62 is used to massage the cheeks, front head and neck areas. The smaller end 64 is used to massage the areas around the eyes and nose.

Figure 4:
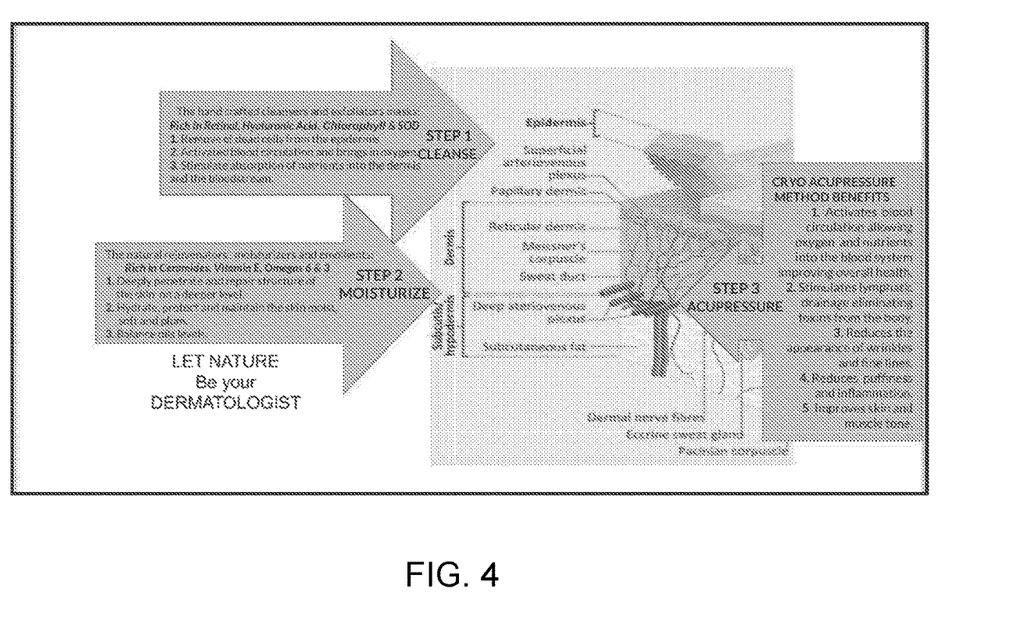
FIG. 4 shows the effect of different materials on different areas of the skin.

FIG. 4 is a depiction of the different layers of skin and the effect that the embodiment has on the various layers of skin. For instance, there is a step one of cleansing for the external layer of skin or the epidermis, there is a moisturizing step two that affects lower layers of skin, and there is a step three of acupressure on the interior layers of skin.

Figure 5:
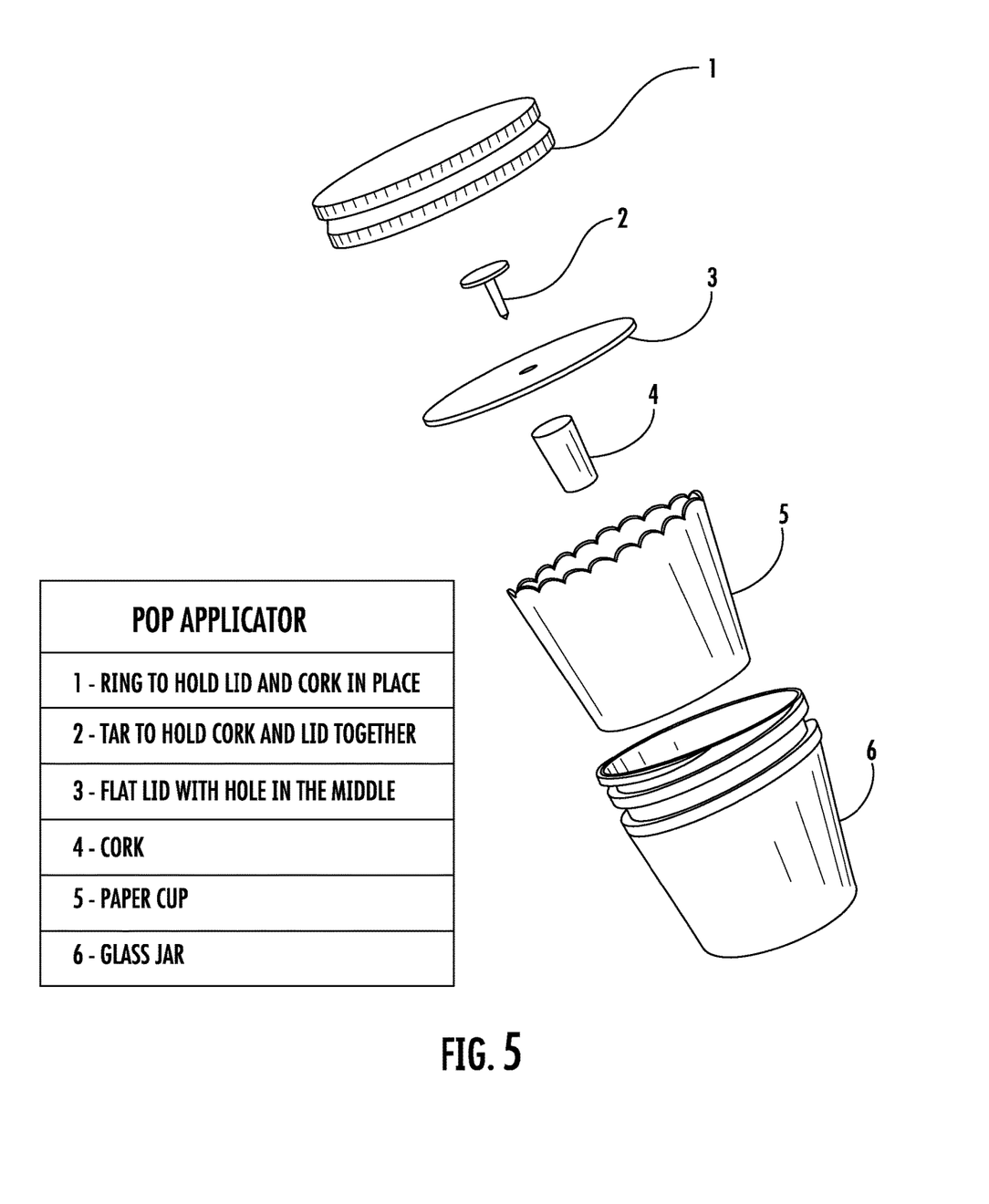
FIG. 5 is a depiction of the pop applicator.

FIG. 5 is an exploded view of the pop applicator in the different components that are utilized in the applicator system.

While cork is the preferred material for the applicator, other non-limiting materials that can be used instead of cork, or in combination with cork, include, thermoplastics thermosets, wood, metal, and composites thereof. The material may be a foam or a solid.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of formulating a skin treatment composition comprising:
obtaining plant components including at least two of wheat grass juice, wheat grass pulp, shea butter, cocoa powder, rice flour, coffee, oil, sugarcane juice, aloe vera, a seed, a fruit, and a vegetable;
blending the plant components;
obtaining a skin treatment applicator that includes a dispensing portion and a handle portion;
placing the blended plant components and the skin treatment applicator in a container; and
freezing the blended plant components to form a frozen skin treatment composition connected to the skin treatment applicator;
wherein the container includes a removable and replaceable lid which encloses the frozen skin treatment composition and the entire skin treatment applicator when not in use, the container being configured to allow for multiple separate applications of the frozen skin treatment composition.

2. The method of claim 1, wherein the step of freezing includes at least one of cryopreservation and flash freezing.

3. The method of claim 1, wherein the step of blending includes incorporating a cryopreservative comprising a plant-based long chain fatty acid.

4. The method of claim 1, wherein the oil comprises at least one of jojoba oil, hemp oil and castor oil.

5. The method of claim 1, wherein, prior to freezing, the plant components include live cells.

6. The method of claim 1, where the skin treatment composition includes at least one member selected from the group consisting of apple, cranberry, pomegranate, potato, watermelon, strawberry, lemon, cucumber, avocado, mango, papaya, kiwi, banana, blueberry, blackberry, goji berries, grapes, cacao seeds, coffee seeds, raw turmeric, raw ginger, beets, raspberry, coconut, pineapple, mangosteen, peaches, cherries, orange, apricot, pumpkin, purple sweet potato, sweet potato, nectarine, raspberry, plum, grapefruit, fig, pear, blackcurrant, cantaloupe, carambola, date fruit, elderberries, guava, honeydew melon, jack fruit, plum, kumquat, lychee, mulberries, passion fruit, kale, spinach, celery, carrot, and pitaya.

7. The method of claim 1, wherein the skin treatment composition includes an exfoliating component configured to remove surface materials from skin, the surface materials including at least one of long-chain natural oils, dead skin cells, and surface dirt.

8. The method of claim 7, where the exfoliating component comprises at least one of micronized fruit pulp and micronized fruit seeds.

9. The method of claim 1, wherein the skin treatment composition comprises plant stem cells.

10. The method of claim 1, wherein the handle portion of the skin treatment applicator comprises cork.

11. The method of claim 1, wherein a first end portion of the skin treatment applicator is encapsulated in the blended plant components prior to freezing.

12. The method of claim 1, further comprising
removing the container from a freezer,
opening the lid of the container,
removing the frozen skin treatment composition, with the applicator connected thereto, from the container, and
applying the frozen skin treatment composition to skin while holding the handle portion of the applicator.

13. A method comprising:
obtaining a blended plant composition including at least two of wheat grass juice, wheat grass pulp, shea butter, cocoa powder, rice flour, coffee, oil, sugarcane juice, aloe vera, a seed, a fruit, and a vegetable;
obtaining a skin treatment applicator that includes a dispensing portion and a handle portion;
placing the blended plant components and the skin treatment applicator in a container;
freezing the blended raw plant components to form a frozen skin treatment composition connected to the skin treatment applicator; and
storing the frozen skin treatment composition and the skin treatment applicator in a container having a removable and replaceable lid that covers the frozen skin treatment composition and the entire applicator and allows for multiple separate applications of the frozen skin treatment composition stored in the container.

14. The method of claim 13, wherein, prior to freezing, the blended plant composition comprises live cells.

15. The method of claim 13, wherein the applicator is intended for multiple applications of the skin treatment composition, and the frozen skin treatment composition is stored in a freezer when not in use.

16. The method of claim 13, wherein the step of applying includes moving an outer surface of the frozen skin treatment composition across a user's skin.

17. The method of claim 13, wherein the step of freezing includes at least one of cryopreservation and flash freezing.

18. The method of claim 1, wherein the frozen skin treatment composition is alcohol-free.

19. The method of claim 1, wherein the lid has an inner surface and an outer surface, and the step of freezing the blended plant components to form a frozen skin treatment composition connected to the skin treatment applicator includes temporarily attaching the applicator to the inner surface of the lid to position the applicator, and
detaching the applicator from the inner surface of the lid after the skin treatment composition is frozen.

20. The method of claim 19, wherein the applicator comprises cork.

* * * * *